United States Patent [19]

Tiffany et al.

[11] Patent Number: 4,684,725

[45] Date of Patent: Aug. 4, 1987

[54] NON-HYGROSCOPIC ADINAZOLAM METHANESULFONATE SALT AND PROCESS THEREFOR

[75] Inventors: Burris D. Tiffany, Portage; Steve Nichols, Vicksburg; Paul A. Meulman, Kalamazoo, all of Mich.; Thomas A. Hylton, Eugene, Oreg.; Michael F. Lipton, Kalamazoo, Mich.

[73] Assignee: The Upjohn Company, Kalamazoo, Mich.

[21] Appl. No.: 757,594

[22] Filed: Jul. 22, 1985

Related U.S. Application Data

[63] Continuation-in-part of Ser. No. 576,042, Feb. 1, 1984, abandoned, and Ser. No. 562,685, Dec. 19, 1983, abandoned.

[51] Int. Cl.$^4$ .................. C07D 487/04; A61K 31/55
[52] U.S. Cl. .................................................. 540/565
[58] Field of Search ...................... 260/245.5; 540/565

[56] References Cited

FOREIGN PATENT DOCUMENTS 146306  6/1985  European Pat. Off. ......... 260/245.5

Primary Examiner—Robert T. Bond
Attorney, Agent, or Firm—Lawrence T. Welch

[57] ABSTRACT

Crystalline, non-hygroscopic adinazolam methanesulfonate, per se, preparable from xylene or preferably from a $C_1$ to $C_2$-alkanol/$C_4$ to $C_6$-alkyl acetate liquid mixture, aids processability of adinazolam methanesulfonate in pharmaceutical production plants.

8 Claims, No Drawings

1

NON-HYGROSCOPIC ADINAZOLAM METHANESULFONATE SALT AND PROCESS THEREFOR

This application is a continuation-in-part of co-pending applications Ser. Nos. 576,042 and 562,685, filed Feb. 1, 1984 and Dec. 19, 1983, respectively, both now abandoned.

INTRODUCTION

This invention provides an improved, commercially efficient process for preparing non-hygroscopic adinazolam methanesulfonate salt in a crystalline form of adinazolam methanesulfonate salt, which are then ready for pharmaceutical formulation into various appropriate dosage administration forms thereof.

BACKGROUND OF THE INVENTION

Adinazolam is now the accepted generic name for 8-chloro-1-(dimethylamino)methyl-6-phenyl-4H-s-triazolo[4,3-a][1,4]benzodiazepine. Adinazolam and its methanesulfonate salt are both described and claimed in Hester, Jr. U.S. Pat. No. 4,250,094, issued Feb. 10, 1981, as well as in various non-U.S. patents of Takeda Chemical Industries of Japan. Adinazolam and its methanesulfonate salt is being clinically studied as a drug candidate for possible use indications of treatment of human patients suffering from acute depression and psychotic disorders including schizophrenia.

Process research chemists and engineers have been asked to find commercially acceptable processes for preparing high quality, stable, non-hygroscopic adinazolam as its methanesulfonic acid salt in substantial yields in high quantity volumes.

The structure of adinazolam has been published for about 10 years, and there have been publications about medical uses, but to our knowledge no one has yet published an efficient process for making adinazolam methanesulfonate in a non-hygroscopic form acceptable for further processing on a commercial scale for pharmaceutical formulations thereof.

To be in a commercially acceptable form the adinazolam methanesulfonate should be in a stable, crystalline form which can be allowed to stand in bulk containers without extensive or hard clumping or aggregation so that it can be readily handled by pharmaceutical plant personnel for pharmaceutical formulation work after periods of storage. Moreover the adinazolam methanesulfonate must be made in a process manner which eliminates or minimizes the possible concern about toxicological safety to plant personnel and ultimately the patient resulting from the use of solvents in its process of preparation and adhering small amounts thereof in the crystal lattice of the adinazolam methanesulfonate product. Chemically, there is also the concern about minimizing yield lowering by-product formation, which could further contaminate the product, due to the method of making the adinazolam methanesulfonate salt, e.g., as a result of the presence of local excesses of methanesulfonic acid, especially in the presence of water which may be introduced with the crystallization solvents or in the crystal lattice of the adinazolam starting material used in the process.

Those in the chemical process development sciences continue to search for new and more efficient processes for making valuable drug compounds, including adinazolam methanesulfonate in stable non-hygroscopic form for extended stability and shelf life purposes.

OBJECTS OF THE INVENTION

It is an object of this invention to provide a process for preparing essentially non-hygroscopic adinazolam methanesulfonate.

It is another object of this invention to provide an improved efficient process for preparing adinazolam as its methanesulfonate salt in a solid, crystal form which is essentially non-hygroscopic.

Another object of the invention is to provide adinazolam methanesulfonate salt, per se, prepared in a non-hygroscopic, crystal form, essentially free of ring-opened by-product, and undesirable solvent residues.

Other objects, aspects and advantages of the invention will become apparent from reading the remaining specification and the claims which follow.

SUMMARY OF THE INVENTION

Briefly, this invention provides adinazolam methanesulfonate per se, in an essentially non-hygroscopic crystal form which is atmosphere-stable as such sitting in bulk containers awaiting formulation into various appropriate pharmaceutical formulations and dosage forms for packaging and ultimate sale months later.

This invention also provides a process for preparing crystalline, essentially non-hygroscopic adinazolam methanesulfonate salt by a process which comprises mixing adinazolam free base into a liquid mixture of a $C_1$ to $C_2$-alkanol and butyl acetate or a $C_4$ to $C_6$-alkyl acetate, e.g., pentyl acetate or hexyl acetate, or mixtures of these compounds, adding methanesulfonic acid diluted in a low boiling liquid such as methanol or ethanol to the above adinazolam mixture in an amount of methanesulfonic acid not to exceed the molar amount of adinazolam in the resulting mixture, heating the resulting mixture to a temperature sufficient to dissolve at least some of the adinazolam in the mixture, to promote formation of adinazolam methanesulfonate salt and for a time sufficient to remove essentially all of the $C_1$ to $C_2$-alkanol and any water in the mixture, cooling the resulting mixture to precipitate and crystallize the adinazolam methanesulfonate from the mixture, and separating the resulting adinazolam methanesulfonate salt from the liquid mixture.

DETAILED DESCRIPTION OF THE INVENTION

This invention provides essentially non-hygroscopic adinazolam methanesulfonate salt, per se, and describes both direct and indirect processes for preparing it. The adinazolam methanesulfonate salt of this invention can be prepared from adinazolam free base or from various hydrated adinazolam acid salt forms, after freeing the adinazolam from any non-methanesulfonate salt forms.

The preferred, direct method for preparing essentially non-hygroscopic adinazolam methanesulfonate comprises mixing from about 1 percent to about 15 percent, by weight, of adinazolam free base into a liquid mixture of butyl acetate or pentyl acetate or hexyl acetate by way of mixture of adinazolam into a $C_1$ to $C_2$-alkanol so that the resulting adinazolam $C_1$ to $C_2$-alkanol/$C_4$ to $C_6$-alkyl acetate mixture is present preferably in a proportion, v/v, of from 1 to 15 parts of the $C_1$ to $C_2$-alkanol to 99 to 85 parts of the $C_4$–$C_6$-alkyl acetate, or mixtures thereof, heating the mixture, if necessary, to effect solution of the adinazolam, adding to the adinazolam in the $C_1$ to $C_2$-alkanol/$C_4$–$C_6$-alkyl acetate or solution the methanesulfonic acid diluted with a $C_1$ to $C_2$-alkanol in a slow controlled manner to minimize localized concentrations of methanesulfonic acid, to an amount just short of stoichiometric equivalency of the methanesulfonic acid relative to the adinazolam concentration in the mixture, and heating the mixture at a temperature sufficient to distill off the methanol or ethanol and essentially all of any water present in the mixture. Heating of these mixtures at a temperature of from about 110° C. to about 120° C. for about 1½ hours to about several hours at atmospheric pressure is sufficient to remove the methanol or ethanol and essentially all of the water present in the mixture.

It has been found that it is necessary to add methanol or ethanol for the adinazolam free base or hydrated methanesulfonate salt thereof to the $C_4$ to $C_6$-alkyl acetate to increase the solubility of the adinazolam in the mixture. The amount of $C_1$ to $C_2$-alkanol added is not critical beyond providing the enhanced solubility property to the solvent mixture because the mixture is heated to distill or azeotrope off the $C_1$ to $C_2$-alkanol and any water in the mixture. Amounts of $C_1$ to $C_2$-alkanol ranging from about 10 to about 15 percent v/v, based upon the amount of $C_4$ to $C_6$-alkyl acetate, are generally sufficient. A solvent mixture containing about a 9:1 v/v $C_4$ to $C_6$-alkyl acetate or to $C_1$ to $C_2$-alkanol, is preferred. Methanol is the preferred $C_1$ to $C_2$-alkanol. Also, maintaining the adinazolam free base concentration in the solvent mixture equal to or higher than the stoichiometric concentration of the methanesulfonic acid helps to ensure reproducibility of high quality, non-hygroscopic adinazolam methanesulfonate salt product yields. Such processing also minimizes formation of the yield lowering ring opened by-products in the mixture, probably due to the combined presence of excess methanesulfonic acid and water in the mixture, which conditions are sought to be avoided herein. The concentration of adinazolam free base or its equivalent hydrated adinazolam methanesulfonate starting material can be mixed with one or the other of the solvent mixture components, and then the other solvent component can be added. The concentration of the adinazolam in the solvent mixture can vary from dilute (concentrations of adinazolam down below or near 1 percent w/v adinazolam in solvent mixture volume) to more concentrated (concentration of adinazolam up near 15 percent w/v, on the same basis as above) for pilot or plant scale operation of the process.

Experiments have been conducted employing fast, one-shot or slow, dropwise, controlled addition of methanesulfonic acid to 1 percent and 10 percent, respectively, of adinazolam free base in a 9:1 v/v butyl acetate/methanol solvent mixture, at 23° C. until the adinazolam/methanesulfonic acid stoichiometric ratio in the mixture reached the indicated ratios, below.

TABLE

| Run | Adinazolam: $H_3CSO_3H$ Ratio | Ring Addition Rate (e) | Ring Opened Impurity (b) |
|---|---|---|---|
| A. 1% Adinazolam/ 1% adinazolam/ volume (a) | | | |
| I. | 1.05 | Fast | $LT^d$ 0.2% |
| II. | 0.83 | Fast | $\sim^d$ 8% |
| III. | 1.00 | Fast | LT 0.2% |
| IV. | 0.91 | Slow | ~6% |
| B. 10% adinazolam/ volume | | | |
| I. | 0.83 | Fast | 3.8% |
| II. | 1.04 | Fast | LT 0.2% |
| III. | 0.92 | Slow | 4.1% |
| IV. (c) | 1.01 | Fast | 0.5% |
| V. | 1.01 | Fast | LT 0.1% |

Footnotes:
(a) All runs conducted in solvent mixture of butyl acetate/methanol
(b) Area percent, based upon adinazolam content
(c) This adinazolam starting material contained 3 percent w/v of N—[[4-(2-benzoyl-4-chlorophenyl)-5-[(dimethylamino)methyl]-4H—1,2,4-triazol-3-yl]methyl]phthalimide
$^d$LT = less than; ~ = about.
(e) Fast = methane sulfonic acid added rapidly in a single portion
Slow = methane sulfonic acid added in a controlled dropwise fashion The studies at the lower concentration levels allowed more uniform sampling of the reaction slurries; the data for the higher concentration studies are more in line with expected plant conditions. Data from both low and higher concentration studies are reasonably consistent; slight variations in the semi-quantitative results can be attributed to non-uniform sampling of the mixtures.

From these data, it is significant that in cases where adinazolam free base was present even in slight excess, relative to the molar content of methanesulfonic acid, the presence of ring-opened impurity in the product was always less than 0.2 percent. A leveling of the amount of ring-opened impurity is seen over time since any localized regions of high methanesulfonic acid acidity are neutralized as the hot slurry thins. The data show that in runs where the methanesulfonic acid is present in excess, relative to the adinazolam free base content, without exception, unacceptably high levels of the ring-opened impurity were found in the isolated adinazolam methanesulfonate product. To avoid problems associated with the presence of ring-opened impurity in isolating the crystalline non-hygroscopic adinazolam methanesulfonate product, therefore, it is desirable to maintain the stoichiometric ratio of methanesulfonic acid to adinazolam in these dehydrating solvent systems to less than 1, that is, the amount of methanesulfonic acid used is deliberately kept slightly lower or no higher than its molar equivalent of adinazolam free base.

As used herein, non-hygroscopic adinazolam methanesulfonate salt is salt which does not have water of hydration in its crystal structure above about 0.15 percent, by weight, or which does not take up water from the atmosphere, or which does not form hard clumps of crystal aggregates of adinazolam methanesulfonate salt upon standing in storage containers awaiting further processing.

Another, but less preferred method or process for preparing non-hygroscopic adinazolam methanesulfonate salt is to dissolve adinazolam free base in methanol, with the aid of heat, if necessary, for the concentration of adinazolam in methanol which is desired, cool the solution to about room temperature, add the methanesulfonic acid in methanol to form the hydrated adinazolam methanesulfonate salt, which precipitates when the mixture is cooled to about 0° C. The precipitated hydrated adinazolam methanesulfonate salt can be separated from the liquid phase and mixed with a high boiling liquid (i.e., a b.p. over about 110° C.) such as xylene, toluene, cyclohexanone, or Skellysolve ®V (a brand of petroleum solvent, which consists essentially of mixed $C_8$ and $C_9$ aliphatic hydrocarbons, boiling at about 240°–290° C.). Xylene is representative of this group. The adinazolam methanesulfonate/high boiling solvent mixture is set for distillation, and the mixture is heated until water or a water/solvent azeotrope ceases to be collected in condensing apparatus connected thereto. Then the mixture is cooled to room temperature or below to precipitate and crystallize the non-hygroscopic adinazolam methanesulfonate salt, which can then be separated and dried by conventional means to a desired degree of dryness.

This latter method is not preferred because approximately 0.1 to about 0.2 percent by weight of xylene or other solvent can be detected in this type of non-hygroscopic adinazolam methanesulfonate salt crystal product. Recent investigations by persons concerned with toxicological and occupational safety have recommended xylene not be used, but that butyl acetate, or a $C_5$ or $C_6$-alkyl acetate would be preferred over the use of the other above named solvents for this recrystallization process. Residual solvent levels of either butyl acetate, or a $C_5$ or $C_6$-alkyl acetate, not exceeding 0.1 percent by weight, thereof, based upon the weight of the adinazolam in the finished non-hydroscopic adinazolam methanesulfonate crystalline product are not considered to represent a significant toxicological hazard at this time. However, efforts should be made to minimize, if not eliminate, the presence of any of these residual solvents.

The invention is further exemplified by the following detailed examples which are not intended to be limiting.

EXAMPLE 1

In a 10 ml. round bottomed flask fitted with a magnetic stir bar and a condenser there was placed 150 mg of hydrated adinazolam methanesulfonate salt and 5 ml. of reagent grade xylene. The stirring mixture was heated in an oil bath over 1.33 hr. to reflux, and maintained at reflux temperature for about 1 hour to remove water from the mixture. The boil bath temperature varied from about 120° C. to 165° C. The resulting mixture was then cooled to 20° C., the adinazolam methanesulfonate solids were removed by filtration, washed with 1 ml. of reagent grade xylene, dried in a vacuum oven at about 50° C. for about 16 hours to constant weight, about 140 mg. The filtration was excellent. The yield of non-hygroscopic adinazolam methanesulfonate was thus about 93 percent; m.p. 242°–245° C., a brown melt.

EXAMPLE 2

This example exemplifies the procedure of Example 1, using xylene, on a larger scale.

To a 1 -liter 3 -necked round-bottom flask there was added 48.98 g. of hydrated adinazolam methanesulfonate and 750 ml. of reagent grade xylene. The slurry was heated and stirred at reflux, about 136° C., for 2 hours. A Dean-Stark trap apparatus was used to azeotropically remove any water present. Only a few drops of water was collected from this batch of adinazolam methanesulfonate starting material. However, the distillate was turbid when cooled. The resulting slurry was cooled over 1.33 hour to about +15° C. and the adinazolam methanesulfonate salt was collected by filtration. The filtration was excellent. The filtered salt was washed with 100 ml. of room temperature xylene. The washed salt was then air dried at room temperature for ten minutes and then dried in a vacuum oven at 102° C. for 136 hours to give 44.55 g., 95 percent recovery of adinazolam methanesulfonate non-hygroscopic salt, m.p. 244°–245° C.

EXAMPLE 3

To a flask apparatus of the type described in Example 1 there was added 150 mg. of hydrated adinazolam methanesulfonate and 5 ml. of reagent grade butyl acetate. The mixture was heated on an oil bath to reflux for about 1 hour and then cooled to 20° C. The solids were collected by filtration, washed with 1 ml. of butyl acetate, and dried in a vacuum oven at about 50° C. for 16 hours to constant weight of 131 mg. The filtration was excellent. The yield was about 87 percent, but with cooling the yield should be about equivalent to that of xylene. The excellent filtration was about comparable to that of the adinazolamethanesulfonate salt from xylene. Butyl acetate or butanol can be used to replace the use of xylene in such crystallization to obtain non-hygroscopic adinazolam methanesulfonate.

EXAMPLE 4

To a 5-liter 3-neck round-bottom flask equipped with a distillation head, a nitrogen gas inlet, an addition funnel, an overhead stirrer and a hot oil bath heating means there was added 300 g. of adinazolam free base, 3.6 liters of n-butyl acetate and 300 ml. of methanol. The resulting mixture was warmed to 30° C. to dissolve all solids. Then, while stirring rapidly, 77.7 g. of methanesulfonic acid was added slowly via the dropping funnel. The resulting mixture was stirred, and the internal temperature of the flask contents was gradually raised to 110° C. while monitoring the amount of methanol distillate coming from the reaction vessel. After 0.5 hours at an internal temperature of 110°–115° C. (with no further observable distillate coming over), a sample of the resulting reaction mixture is removed, the solid salt thereof is isolated, and its melting point is checked. Any melting activity in the temperature range of 180°–195° C. indicates incomplete conversion of adinazolam to its desired non-hygroscopic adinazolam methanesulfonate salt form. When the melting point of the solid salt sample is in the range of 242°–246° C., the salt forming reaction and crystal form interchange is complete.

When the reaction is complete, the resulting mixture is cooled to ambient temperature, filtered to separate the solid adinazolam methanesulfonate non-hygroscopic salt product, washed with butyl acetate and dried in a vacuum oven at 50° C. overnight. The resulting non-hygroscopic adinazolam methanesulfonate salt is profile quality, at least 99.6 percent pure by high pressure liquid chromatography analyses means. The yield is about 361 g., 98 percent, based on methanesulfonic acid.

EXAMPLE 5 LARGE SCALE

To a large reaction vessel, there is charged 4.44 kg. (12.61 moles) of adinazolam free base. The atmosphere of the vessel is rendered inert by removing air therefrom with a nitrogen gas flow and then 60 kg. of methanol is pulled into the inerted reaction vessel. The resulting mixture is heated to 40° C. whereupon a solution develops. The solution is filtered at 40° C. through a sterile filter pad followed by a 2 gallon methanol rinse. The filtered solution is transferred back into the clean reaction vessel, cooled to 25° C. and then treated over 5 minutes with a solution of 1,263 g. (13.14 mole) of methanesulfonic acid in 7.3 liters of methanol. At the end of the addition of the methanesulfonic acid solution, the mixture is cooled to 0° C. is begun. After about 10 minutes of coolng a white precipitate will be observed which thickens somewhat and then thins out. The reactor vessel contents are filtered at 0° C. to a damp filter cake. The filter cake (hygroscopic form of adinazolam methanesulfonate salt) is transferred back to the reaction vessel and mixed with 25–30 gallons of xylene. The resulting mixture in the vessel is set for distillation, and the mixture is heated and distilled (with the use free of free steam in the vessel jacket, and then with pressure steam in the vessel jacket) until the reaction vessel pot temperature is 135° C. Distillation starts at about 70° C. with a water/xylene azeotrope distillate. At 135° C., the reaction vessel and its contents are switched to a reflux mode and refluxed for 0.5 hour at 135° C. The contents of the reaction vessel are then cooled slowly to room temperature. The contents of the vessel are then filtered and washed with 3 gallons of Skellysolve ®B brand of mixed hexanes. The filtered solids, non-hygroscopic adinazolam methanesulfonate salt are dried in vacuo at 70° C. for 2 days. The yield of non-hygroscopic adinazolam methanesulfonate salt from this procedure is about 4.44 to 78.6 percent. The characteristic non-hygroscopic form of adinazolam methanesulfonate is shown by an infrared (IR) spectrum of a sample of this salt form product.

EXAMPLE 6 LARGE SCALE, PREFERRED PROCESS

To a large, pilot plant scale, stainless steel reactor vessel, from which air is removed with nitrogen gas, there is added 9.2 kg. of adinazolam free base via the reactor manhole, while using a ventilation duct. The chemical operator should use gloves, a respirator and face shield protection equipment. The reactor manhole cover is closed and the reactor vessel is evacuated of air by flushing with nitrogen. Then 96.8 kg. of n-butyl acetate is pulled into the reactor vessel by vacuum from a grounded drum. Then 7.3 kg. of absolute methanol is pulled into the reactor vessel from a grounded drum. The reactor vessel contents are stirred and heated to 35° C. to dissolve the adinazolam solids in the mixture. While continuing to heat the mixture 2.382 kg. of methanesulfonic acid is pulled into the reaction vessel with vacuum from a glass bottle connected with polyethylene tubing. The vacuum is broken with nitrogen gas.

The resulting mixture is stirred rapidly (the mixture becomes thick), and is heated slowly to 110° C. while methanol and any water in the mixture is distilled off.

After 2 hours of heating the stirred mixture at 110° C. a sample of the reaction mixture is taken and checked by melting point for completion of the reaction. When the melting point of the adinazolam methanesulfonate salt in the sample is 242°–246° C., the reaction is considered complete. The solids should be free-flowing and settle quickly when the reaction is complete and stirring is discontinued.

The resulting reaction mixture is cooled to room temperature and the solids are filtered via a 20-inch stainless steel, grounded filter. The filtered solids are rinsed with butyl acetate. The resulting crystalline adinazolam methanesulfonate salt is dried in a vacuum oven at 50° C. for three days. The yield of non-hygroscopic adinazolam methanesulfonate is 11.0 kg. (94 percent yield).

We claim:

1. A process for preparing crystalline essentially non-hygroscopic adinazolam methanesulfonate which comprises mixing adinazolam free base into a liquid mixture of a $C_1$ to $C_2$-alkanol and a $C_4$ to $C_6$-alkyl acetate, or mixtures thereof, adding methanesulfonic acid diluted in a low boiling liquid to the above adinazolam mixture in an amount of methanesulfonic acid not to exceed the molar amount of adinazolam in the resulting mixture, heating the resulting mixture to a temperature sufficient to dissolve at least some of the adinazolam in the mixture, to promote formation of the adinazolam methanesulfonate salt, and for a time sufficient to remove essentially all of the $C_1$ to $C_2$-alkanol and any water in the mixture, cooling the resulting mixture to precipitate and crystallize the adinazolam methanesulfonate from the mixture, and separating the resulting adinazolam methanesulfonate salt from the liquid phase.

2. A process according to claim 1 wherein the concentration of the adinazolam free base in the liquid mixture is from about 1 to about 15 percent by weight, based upon the weight of the liquid mixture.

3. A process according to claim 2 where the adinazolam free base is dissolved in a methanol/butyl acetate mixture in the process.

4. A process according to claim 3 wherein the final butyl acetate/methanol volume ratio in the liquid mixture is about 8 to 1 to 12 to 1 v/v butyl acetate to methanol.

5. A process according to claim 4 wherein the final butyl acetate to methanol volume ratio is about 10:1 v/v butyl acetate to methanol in the liquid mixture.

6. A process which comprises dissolving hydrated adinazolam methanesulfonate salt in a mixture of a $C_1$ to $C_2$-alkanol and a $C_4$ to $C_6$-alkyl acetate, or mixtures thereof heating the mixture to a temperature sufficient to remove the $C_1$ to $C_2$-alkanol and any water in the mixture, cooling the mixture to crystallize the adinazolam methanesulfonate salt, and separating the adinazolam methanesulfonate salt from the liquid phase of said mixture.

7. A process according to claim 6 wherein the $C_1$ to $C_2$-alkanol is methanol, and a mixture of methanol/butyl acetate is used to dissolve the hydrated adinazolam methanesulfonate salt therein.

8. Crystalline adinazolam methanesulfonate which is essentially non-hygroscopic.

* * * * *